United States Patent [19]

Crossley

[11] Patent Number: 4,593,111

[45] Date of Patent: Jun. 3, 1986

[54] SILYL ISOTHIOCYANATES

[75] Inventor: Roger Crossley, Reading, England

[73] Assignee: John Wyeth & Brother Ltd., Maidenhead, England

[21] Appl. No.: 737,980

[22] Filed: May 24, 1985

Related U.S. Application Data

[63] Continuation-in-part of Ser. No. 506,278, Jun. 21, 1983, Pat. No. 4,539,406.

[30] Foreign Application Priority Data

Jun. 25, 1982 [GB] United Kingdom ............... 8218464

[51] Int. Cl.$^4$ ............................. C07F 7/10; C07F 7/18
[52] U.S. Cl. .................................. 556/410; 556/411; 546/14; 548/110
[58] Field of Search ................. 556/410, 411; 546/14; 548/110

[56] References Cited

U.S. PATENT DOCUMENTS

| | | | |
|---|---|---|---|
| 4,000,142 | 12/1976 | Curran et al. | 260/287 T |
| 4,046,895 | 9/1977 | Curran et al. | 424/258 |
| 4,405,803 | 9/1983 | Fauss | 556/410 |
| 4,435,587 | 3/1984 | Sugiyama et al. | 556/410 |

FOREIGN PATENT DOCUMENTS 1463666  2/1977  United Kingdom ............ 260/287 T

OTHER PUBLICATIONS

Chemical Abstract 87:68430s.
Chemical Abstract 86:16786x.

Primary Examiner—Paul F. Shaver
Attorney, Agent, or Firm—Richard K. Jackson

[57] ABSTRACT

The invention concerns novel compounds of formula IIIA $$R_x{}^a Si(NCS)_{4-x} \qquad \text{IIIA}$$

wherein $R^a$ is selected from electron donating substituents consisting of alkoxy of 1–10 carbon atoms, cycloalkoxy of 4–8 carbon atoms, aralkoxy of 7–12 carbon atoms, phenoxy which may be substituted by alkyl of 1–10 carbon atoms, alkoxy of 1–10 carbon atoms or trifluoromethyl, the group $R^b R^c$N-wherein $R^b$ and $R^c$ are selected from alkyl of 1–6 carbon atoms, cycloalkyl of 4–6 carbon atoms, phenyl which may be substituted by alkyl of 1–10 carbon atoms, alkoxy of 1–10 carbon atoms or trifluoromethyl, and aralkyl of 7–12 carbon atoms or $R^b$ and $R^c$ may be joined to form a pyrrolidinyl or piperidinyl ring with the nitrogen atom, which ring may be substituted by alkyl of 1–10 carbon atoms; alkylthio of 1–10 carbon atoms, cycloalkylthio of 4–8 carbon atoms, aralkylthio of 7–12 carbon atoms, phenylthio which may be substituted by alkyl of 1–10 carbon atoms, alkoxy of 1–10 carbon atoms, or trifluoromethyl, and hydrocarbon substituents selected from alkyl of 1–10 carbon atoms, cycloalkyl of 4–8 carbon atoms, aralkyl of 7–12 carbon atoms, or phenyl which may be substituted by alkyl of 1–10 carbon atoms, alkoxy of 1–10 carbon atoms or trifluoromethyl, at least one group $R^a$ being an electron donating substituent with the provisos that:

(i) when x is 3 and all three $R^a$ groups are the same alkoxy then the alkoxy group has at least 3 carbon atoms;
(ii) when $R^a$ is alkoxy and x is 1 then $R^a$ is other than propoxy;
(iii) when one or more $R^a$ are alkylthio and the others (if any) are alkyl then the alkylthio group has at least 2 carbon atoms;
(iv) when $R^a$ is aryloxy and x is 3 then at least one group $R^a$ is other than aryloxy.

The compounds are useful intermediates in an improved process for preparing fused carbocyclic ring derivatives of pyridine especially 5,6,7,8-tetrahydroquinoline 8-nitriles and thioamides which is described in co-pending U.S. Ser. No. 506,278. The nitriles and thioamides are anti-ulcer and/or anti-secretory agents.

8 Claims, No Drawings

SILYL ISOTHIOCYANATES

The invention relates to intermediates useful in a new process for preparing fused carbocyclic ring derivatives of pyridine which is described and claimed in U.S. Ser. No. 506,278 filed June 21st, 1983, now U.S. Pat. No. 4,539,406. This application is a continuation-in-part of Ser. No. 506,278.

In or United Kingdom patent specification No. 1463666 we described a process for preparing tetrahydroquinoline-8-thiocarboxamides, nitriles and carboxamides and related compounds by treating a corresponding sodio, lithio, potassio or magnesium halide derivative with a silyl compound of formula $R_xSi(NCY)_{4-x}$ wherein R is alkyl, aryl or aralkyl, Y is oxygen or sulphur and x has a value from 0 to 3 and subjecting the product to hydrolysis or alcoholysis. The reaction is conducted under anhydrous conditions preferably in an inert solvent for example a hydrocarbon solvent such as benzene, toluene or n-hexane. It is also stated in that patent specification that ethers, including cyclic ethers such as tetrahydrofuran should be avoided.

We have now surprisingly found that ethers can be used as solvents if the silyl reagent is modified to contain an alkoxy group or other electron donating substituent. Our new process can also be used to prepare compounds related to those described in patent specification No. 1463666. The new reagents can also be used in the same solvents described in UK specification No. 1463666. The new process is described and claimed in our co-pending U.S. Ser. No. 506,278.

This invention provides novel intermediates useful in the process of U.S. Ser. No. 506,278 for preparing inter alia thioamides and nitriles of formula I

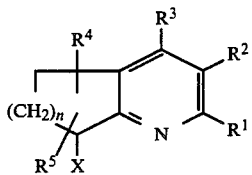

or acid addition salts thereof, wherein $R^1$, $R^2$, $R^3$, $R^4$ and $R^5$ are the same or different and represent hydrogen or alkyl of 1-6 carbon atoms, cycloalkyl of 4-6 carbon atoms, aralkyl of 7-12 carbon atoms or phenyl groups any of which groups may be substituted by alkyl of 1-6 carbon atoms, alkoxy of 1-6 carbon atoms or trifluoromethyl, or $R^1$ and $R^2$ taken together, or $R^2$ and $R^3$ taken together form a 5,6, or 7 membered carbocyclic ring which may be saturated or unsaturated, and when $R^1$ and $R^2$ form a ring, the ring has the same number of carbon atoms as the ring carrying X, $R^4$ and $R^5$ may also represent alkoxy of 1-6 carbon atoms, n is 1,2 or 3 and X is CN, or $CSNH_2$ which process comprises treating a compound of formula II

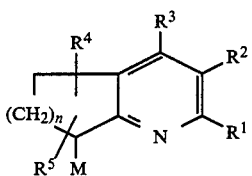

wherein $R^1$, $R^2$, $R^3$, $R^4$, $R^5$ and n are as defined in connection with formula I, and M is sodium, potassium, lithium, or MgHal, where Hal is chlorine, bromine or iodine, with a silyl compound of formula III, $R_x{}^aSi(NCS)_{4-x}$ wherein $R^a$ is selected from electron donating substituents consisting of alkoxy of 1-10 carbon atoms, cycloalkoxy of 4-8 carbon atoms, aralkoxy of 7-12 carbon atoms, phenoxy which may be substituted by alkyl of 1-10 carbon atoms, alkoxy of 1-10 carbon atoms, or trifluoromethyl, the group $R^bR^cN-$ wherein $R^b$ and $R^c$ are selected from alkyl of 1-6 carbon atoms, cycloalkyl of 4-6 carbon atoms, phenyl which may be substituted by alkyl of 1-10 carbon atoms, alkoxy of 1-10 carbon atoms, or trifluoromethyl, and aralkyl of 7-12 carbon atoms or $R^b$ and $R^3$ may be joined to form a pyrrolidinyl or piperidinyl ring with the nitrogen atom, which ring may be substituted by alkyl of 1-10 carbon atoms; alkylthio of 1-10 carbon atoms, cycloalkylthio of 4-8 carbon atoms, aralkylthio of 7-12 carbon atoms, phenylthio which may be substituted by alkyl of 1-10 carbon atoms, alkoxy of 1-10 carbon atoms or trifluoromethyl, and hydrocarbon substituents selected from alkyl of 1-10 carbon atoms, cycloalkyl of 4-8 carbon atoms, aralkyl of 7-12 carbon atoms or phenyl, which may be substituted by $C_{1-10}$ alkyl, $C_{1-10}$ alkoxy or trifluoromethyl, at least group $R^a$ being an electron donating substituent, x has a value from 1 to 3, then subjecting the product to hydrolysis or alcoholysis, with the proviso that when a compound of formula I in which X is CN is desired the molar ratio of compound $R_x{}^aSi(NCS)_{4-x}$ to compound II is at least 2:1 and x is 3 and if desired isolating the product as an acid addition salt.

The compound of formula I and II are, in general, known compounds which are described in UK patent specification Nos. 1463666, 1432378, 1463668, 1465651 and 1495993 or are analogous to compounds described therein. Compounds of formula II in which M is MgHal are also described in UK Pat. No. 1463665 or are analogous to compounds described therein. The compounds of formula I in which X is $CSNH_2$ are anti-ulcer agents which display anti-ulcer and/or anti-secretory activity in standard test procedures. The nitriles of formula I where X is CN are intermediates for the corresponding thioamides and usually also display anti-ulcer and/or anti-secretory activity.

In general the preferred reaction medium for the process of U.S. Ser. No. 506,278 comprises an ether solvent e.g., a dialkyl ether, wherein the alkyl group has from 1 to 6 carbon atoms e.g., diethyl ether or a cyclic ether such as tetrahydrofuran or dioxan. Other reaction media which may be used are hydrocarbon solvents such as benzene, toluene or n-hexane, or mixtures of two or more of the above mentioned solvents.

Preferably at least one electron donating group $R^a$ is alkoxy of 1-10 carbon atoms, cycloalkoxy of 4-8 carbon atoms, aryloxy of 7-12 carbon atoms or di($C_1$-$C_6$ alkyl) amino. Good results have been obtained with a silyl compound of formula $R_3{}^1SiNCS$ wherein one group $R^a$ is lower alkoxy or aryloxy and the other two are lower alkyl e.g., methoxydimethylsilyl isothiocyanate
isopropoxydimethylsilyl isothiocyanate
2,6-di-t-butyl-4-methylphenoxydimethylsilyl isothiocyanate.

However two or all three of the $R^a$ groups may be alkoxy e.g., trimethoxy or triethoxy, or dialkylamino e.g. dimethylamino. Branched chain alkoxy or aryloxy groups are preferred. A particularly useful compound III is tri(dimethylamino)silyl isothiocyanate. $R^a$ may have from 1–10 carbon atoms when alkyl or alkylthio.

When any of $R^1$, $R^2$, $R^3$, $R^4$, $R^5$, $R^a$, $R^b$ or $R^c$ is an alkyl radical it is preferred that this is a lower alkyl radical of 1 to 6 carbon atoms which may have a straight or branched chain e.g., methyl, ethyl, n- and iso-propyl and n-, and t-butyl. When $R^4$, $R^5$, or $R^a$ is an alkoxy radical it is preferred that the radical is lower alkoxy in which the alkyl portion has 1 to 6 carbon atoms and is as defined above, for an alkyl radical. Similarly when $R^a$ is an alkylthio group the alkyl portion is as defined for an alkyl group.

When any of $R^1$, $R^2$, $R^3$, $R^4$, $R^5$, $R^a$, $R^b$ or $R^c$ is a cycloalkyl radical such radicals having from 4 to 6 carbon atoms are preferred i.e., cyclobutyl, cyclopentyl or cyclohexyl. If $R^a$ is cycloalkoxy or cycloalkylthio the cycloalkyl portion of this group preferably has from 4 to 8 carbon atoms but maybe as just described for a cycloalkyl group.

An aralkyl group may be an arylalkyl group in which the alkyl portion is as described herein for an alkyl group. Preferred aralkyl groups are those having from 7–12 carbon atoms.

An aralkyloxy group may be such a group in which the aralkyl portion is as just described for an aralkyl group. The aryl portion is preferably phenyl.

When any of $R^1$, $R^2$, $R^3$, $R^4$, $R^5$, $R^a$, $R^b$ or $R^c$ is an aryl group it is preferably phenyl or substituted phenyl (substituted by e.g., alkyl, alkoxy, or trifluoromethyl). Similarly an aryloxy or arylthio group may be such a group in which the aryl portion is as defined for an aryl group, 2,6-disubstituted phenyl being a preferred group.

Apart from the question of solvent, already discussed above, the reaction of U.S. Ser. No. 506,278 may be carried out as described generally in UK patent specification No. 1463666. Conveniently the starting material of formula II is prepared in situ by reaction of a compound of formula II, wherein M is hydrogen with a suitable organometallic compound such as an alkyl, aryl or aralkyl lithium, sodium or potassium compound as described in UK patent specification No.1432378 or using the improvement described in UK patent specification No. 1463666, wherein a metal amide is reacted with a compound of formula II wherein M is hydrogen. The metal amide may be formed in situ and may be any of those described in UK patent specification No. 1463666 viz. an amide derived from a secondary amine such as a dialkylamine e.g., diethylamine, di-isopropylamine, ditertiary butylamine, di-n-decylamine, dicyclohexylamine, N-t-amyl N-t-butylamine, N-isopropyl-N-cyclohexylamine, or N(1-ethylcyclohexyl)-1,1,3,3-tetramethylbutylamine or a cyclic compound e.g., piperidine, or 2,2,6,6, tetramethylpiperidine. Alternatively any of the metal amides described in co-pending U.S. Ser. No. 472787 filed 7th March 1983 may be used. These metal amides have the formula IV

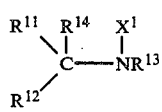

IV wherein $R^{14}$ is a straight or branched chain alkyl group of 1 to 6 carbon atoms or an aryl group, $R^{11}$ is hydrogen, aryl or a tertiary alkyl group of 4–6 carbon atoms, $R^{12}$ is aryl or a tertiary alkyl group of 4–6 carbon atoms, $R^{13}$ is a branched chain alkyl of 3 to 6 carbon atoms; $X^1$ is lithium, sodium or potassium. These metal amides are conveniently prepared by a novel process described in U.S. Ser. No. 472787, namely reacting a compound of formula V

V wherein $R^{11}$, $R^{12}$ and $R^{13}$ are as defined above with a metal alkyl $MR^{14}$ where $R^{14}$ is as defined above and M is lithium, sodium or potassium, in an inert non-polar solvent to obtain a compound of formula IV.

A particularly preferred compound of formula IV is lithium of N-t-butyl-N-(1-phenylpentyl)amide.

The starting compounds of formula II, wherein X is MgHal may be prepared by the general method described in UK patent specification No. 1463665. However, in our UK specification No. 1463666 it is said that the ether solvent has to be removed and the reaction with the silyl compound conducted in a different solvent. Since the process of the U.S. Ser. No. 506,278 can be conducted in ethers it is not usually necessary to remove the ether when the MgHal compound II has been prepared in an ether solvent.

The silyl compounds of formula III which are used in the process of U.S. Ser. No. 506,278 may be prepared by reacting a thiocyanate, such an ammonium thiocyanate, with a silyl halide, $R_x^a SiHal_{4-x}$ e.g., $R_3^a$ SiHal where $R^a$ is as defined above and Hal is chlorine or bromine.

Some of the silyl isothiocyanates of formula III are novel compounds and the novel compounds comprise the present invention. They have formula IIIa.

$$R_x^a Si(NCS)_{4-x} \qquad \text{IIIa}$$

wherein $R^a$ and x are as defined in connection with formula III with the provisos that (i) when x is 3 and all three $R^a$ groups are the same alkoxy then the alkoxy group has at least 3 carbon atoms;

(ii) when $R^a$ is alkoxy and x is 1 then $R^a$ is other than propoxy;

(iii) when one or more $R^a$ are alkylthio and the others (if any) are alkyl then the alkylthio group has at least 2 carbon atoms;

(iv) when $R^a$ is aryloxy and x is 3 then at least one group $R^a$ is other than aryloxy.

Novel compounds of the invention include compounds of formula IIIa, wherein one or two groups $R^a$ are alkoxy or aryloxy and another group $R^a$ is alkyl and x is 3 e.g., $Me_2(OMe)SiNCS$
$Me_2(OiPr)SiNCS$
$Me(OMe)_2SiNCS$
2,6,di-t-butyl--4-methylphenoxy(me)$_2$SiNCS and where one or more groups $R^a$ are dialkylamino e.g., $(Me_2N)_3SiNCS$.

The compounds of formula III (including the novel compounds of formula IIIa) may be prepared by reacting a silyhalide $R_x^a Si(Hal)_{4-x}$, wherein Hal is chlorine, bromine or iodine, preferably chlorine, ($R^a$ and x being as defined above) with a thiocyanate e.g., ammonium thiocyanate. Methods of preparing the novel compounds of formula III are included in the invention.

The silylhalides are known or may be prepared by methods known for analogous compounds.

The following Examples illustrate the invention.

EXAMPLE 1

Preparation of silyl isothiocyanates

General Method

Ammonium thiocyanate (1.1 molar equivalents) in cyclohexane (100 ml) was refluxed with stirring under a Dean-Stark apparatus until water had been removed. The suspension was cooled and treated with a silyl chloride (50 g) and the mixture was heated at reflux with stirring until the reaction was complete (usually 24 hour) Precipitated ammonium chloride was removed by filtration and the product purified by distillation. In this manner were prepared the following:

|     | Silyl chloride | Silylisothiocyanate | bp/mm | Yield |
|-----|----------------|---------------------|-------|-------|
| (a) | $Me_2(OMe)SiCl$ | $Me_2(OMe)SiNCS$ | 148° C./760 | 68% |
| (b) | $Me_2(OiPr)SiCl$ | $Me_2(OiPr)SiNCS$ | 68° C./15 | 79% |
| (c) | $Me(OMe)_2SiCl$ | $Me(OMe)_2SiNCS$ | 58° C./15 | 66% |
| (d) | $(OEt)_3SiCl$ | $(OEt)_3SiNCS$ | 98° C./15 | 95% |
| (e) | $(Me_2N)_3SiCl$ | $(Me_2N)_3SiNCS$ | 140° C./15 | 15% |

EXAMPLE 2

Reaction of silylisothiocyanates with tetrahydroquinolines

General Method

A 5,6,7,8-tetrahydroquinoline (0.01 mole) in the solvent indicated (approx. 15 ml) at 0° C. under nitrogen was treated with an alkyl lithium or a lithium amide (0.01 mole). To this solution of the 5,6,7,8-tetrahydro-8-lithioquinoline was added, at around 0° C. under nitrogen, the silyl isothiocyanate (0.01 mole) and the mixture was stirred 15 minutes. $H_2O$ (10 ml) and 2N HCl (15 ml) were added and the acid layer was separated and washed with ethyl acetate. The aqueous solution was basified ($Na_2CO_3$) and extracted with chloroform. The chloroform extracts were dried ($MgSO_4$) and evaporated to give the 5,6,7,8-tetrahydroquinoline-8-thiocarboxamide. In this manner the thioamides in the table were prepared.

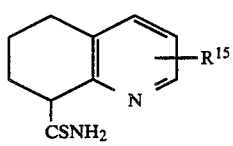

| Expt. | $R^{15}$ | Silyl Derivatives | Solvent | Base | Yield (n.m.r) |
|-------|------|-------------------|---------|------|--------|
| (a) | 3-Me | $Me_2Si(OMe)NCS$ | THF | n-BuLi | 5% |
| (b) | 3-Me | $Me_2Si(OiPr)NCS$ | THF | n-BuLi | 30–35% |
| (c) | 3-Me | $Me_2Si(OiPr)NCS$ | toluene | n-BuLi | 15% |
| (d) | 4-Me | $Me_2Si(OiPr)NCS$ | toluene | n-BuLi | 5% |
| (e) | 4-Me | $Me_2Si(OiPr)NCS$ | THF | n-BuLi | 10% |
| (f) | 4-Me | $Me_2Si(OiPr)NCS$ | toluene |  Ph-N(Bu)-Li | 20% |
| (g) | 4-Me | $Me_2Si(OiPr)NCS$ | THF | " | 25% |
| (h) | 3-Me | $(EtO)_3SiNCS$ | THF | n-BuLi | 10% |
| (i) | 3-Me | $Me(OMe)_2SiNCS$ | THF | n-BuLi | 10% |
| (j) | 3-Me | $(Me_2N)_3SiNCS$ | THF | n-BuLi | 40% |

| Expt. | $R^{15}$ | Silyl Derivatives | Solvent | Base | Yield (n.m.r) |
|-------|------|-------------------|---------|------|--------|
| (k) | 3-Me | 2,6-di-t-Bu-4-Me-C$_6$H$_2$-O-SiNCS(Me$_2$) | THF | n-BuLi | 50% |

No product was obtained when the above reactions were carried out using $Me_3SiNCS$ in tetrahydrofuran (THF) instead of the named silyl derivative.

EXAMPLE 3

(a)

2,6-Di-t-butyl-4-methylphenoxydimethylchlorosilane

A mixture of 2,6-di-t-butyl-4-methylphenol (110 g, 0.5M), acetonitrile (500 ml), triethylamine (70 ml, 0.5M) and dichlorodimethylsilane (61 ml, 0.5M) was refluxed for 16 hours. The solvent was evaporated and the residue extracted with toluene (500 ml). The toluene extract was evaporated and the residue recrystallised from acetonitrile to give the title compound (90 g, 57%) m.p. 119°–121° (Found: C, 65 65; H, 9.4%. $C_{17}H_{29}ClOSi$ requires C, 65.2; H, 9.3%).

(b) 2,6-Di-t-butyl-4-methylphenoxydimethylsilyl isothiocyanate

A mixture of the silyl chloride prepared in (a) above (78 g, 0.25M), ammonium thiocyanate (26 g, 0.28M) and toluene was refluxed for 48 hours. The mixture was filtered and the filtrate evaporated; recrystallisation of the residue from acetonitrile gave the title compound (40 g, 48%) m.p. 83°–4°. (Found: C, 64.8; H, 9.0; N, 4.05. $C_{18}H_{29}$ NOSSi requires: C, 64.4; H, 8.7; 4.2.)

I claim:

1. A compound of formula IIIA $$R_x^a Si(NCS)_{3-x} \qquad \text{IIIA}$$

wherein $R^a$ is selected from electron donating substituents consisting of alkoxy of 1–10 carbon atoms, cycloalkoxy of 4–8 carbon atoms, aralkoxy of 7–12 carbon atoms, phenoxy, which may be substituted by alkyl of 1–10 carbon atoms, alkoxy of 1–10 carbon atoms or trifluoromethyl, the group $R^b R^c N$-wherein $R^b$ and $R^3$ are selected from alkyl of 1–6 carbon atoms, cycloalkyl of 4–6 carbon atoms, phenyl which may be substituted by alkyl of 1–10 carbon atoms, alkoxy of 1–10 carbon atoms or trifluoromethyl, and aralkyl of 7–12 carbon atoms or $R^b$ and $R^c$ may be joined to form a pyrrolidinyl or piperidinyl ring with the nitrogen atom, which ring may be substituted to alkyl of 1–10 carbon atoms; alkylthio of 1–10 carbon atoms, cycloalkylthio of 4–8 carbon atoms, aralkylthio of 7–12 carbon atoms, phenylthio which may be substituted by alkyl of 1–10 carbon atoms, alkoxy of 1–10 carbon atoms or trifluoromethyl, and hydrocarbon substituents selected from alkyl of 1–10 carbon atoms, cycloalkyl of 4–8 carbon atoms, aralkyl of 7–12 carbon atoms, or phenyl which may be substituted by alkyl of 1–10 carbon atoms, alkoxy of 1–10 carbon atoms or trifluoromethyl, at least one group $R^a$ being an electron donating substituent, with the provisos that:

(i) when x is 3 and all three $R^a$ groups are the same alkoxy then the alkoxy group has at least 3 carbon atoms;

(ii) when $R^a$ is alkoxy and x is 1 then $R^a$ is other than propoxy;

(iii) when one or more $R^a$ are alkylthio and the others (if any) are alkyl then the alkylthio group has at least 2 carbon atoms;

(iv) when $R^a$ is aryloxy and x is 3 then at least one group $R^a$ is other than aryloxy.

2. A compound of formula IIIA as claimed in claim , wherein one or two groups $R^a$ are alkoxy or aryloxy, another group $R^a$ is alkyl and x is 3.

3. A compound of formula IIIA as claimed in claim 2, wherein one or more groups $R^a$ are di-$C_1$-$C_6$-alkylamino.

4. Dimethylmethoxysilyl isothiocyanate.

5. Dimethylisopropoxysilyl isothiocyanate.

6. Methyldimethoxysilyl isothiocyanate.

7. 2,6,Di-t-butyl-4-methylphenoxy, dimethylsilyl isothiocyanate.

8. Tri(dimethylamino)silyl isothiocyanate.

* * * * *

UNITED STATES PATENT AND TRADEMARK OFFICE
CERTIFICATE OF CORRECTION

PATENT NO. : 4,593,111

DATED : June 3, 1986

INVENTOR(S) : Roger Crossley

It is certified that error appears in the above-identified patent and that said Letters Patent are hereby corrected as shown below:

Column 2, line 13, delete "$R^3$" and insert --$R^c$--;

Column 2, line 59, delete "$R_3^1$" and insert --$R_3^a$--;

Column 4, line 57, delete "$(me)_2$" and insert --$(Me)_2$--;

Column 6, Claim 1, in the formula at line 49, delete the subscript "3-x" and insert --4-x--;

Column 6, Claim 1, line 56, delete "$R^3$" and insert --$R^c$--;

UNITED STATES PATENT AND TRADEMARK OFFICE
CERTIFICATE OF CORRECTION

PATENT NO. : 4,593,111
DATED : June 3, 1986
INVENTOR(S) : Roger Crossley

It is certified that error appears in the above-identified patent and that said Letters Patent is hereby corrected as shown below:

Column 6, Claim 1, line 63, delete "to" and insert --by--;
Column 8, Claim 2, line 3, after "claim", insert --1--.

Signed and Sealed this

Twenty-third Day of September 1986

[SEAL]

Attest:

DONALD J. QUIGG

Attesting Officer

Commissioner of Patents and Trademarks